United States Patent [19]

Melera et al.

[11] Patent Number: 5,332,815

[45] Date of Patent: Jul. 26, 1994

[54] PROCESS FOR THE PREPARATION OF ALKALINE EARTH METAL SALTS OF (6R)-N(10)-FORMYL-5,6,7,8-TETRAHYDROFOLIC ACID

[75] Inventors: Attilio Melera, Montagnola; Fabrizio Marazza, Sorengo, both of Switzerland

[73] Assignee: Sapec S.A. fine chemicals, Lugano, Switzerland

[21] Appl. No.: 955,445

[22] Filed: Oct. 2, 1992

[30] Foreign Application Priority Data

Oct. 4, 1991 [CH] Switzerland ............... 2933/91

[51] Int. Cl.$^5$ ........................................... C07D 475/04
[52] U.S. Cl. ................................... 544/258; 544/251
[58] Field of Search ..................... 544/258; 514/549

[56] References Cited

U.S. PATENT DOCUMENTS

| 4,148,999 | 4/1979 | Temple | 544/258 |
| 5,006,655 | 4/1991 | Müller et al. | 544/258 |
| 5,010,194 | 4/1991 | Müller et al. | 544/258 |
| 5,134,235 | 7/1992 | Mueller et al. | 544/258 |
| 5,194,611 | 3/1993 | Marazza et al. | 544/258 |
| 5,239,074 | 8/1993 | Marazza et al. | 544/247 |

FOREIGN PATENT DOCUMENTS

| 455013 | 11/1991 | European Pat. Off. | 544/258 |
| 90-09382 | 8/1990 | PCT Int'l Appl. | 544/258 |
| 305574 | 5/1955 | Switzerland | 544/258 |
| 709574 | 5/1954 | United Kingdom | 544/258 |

*Primary Examiner*—Donald G. Daus
*Attorney, Agent, or Firm*—Burns, Doane, Swecker & Mathis

[57] ABSTRACT

A process for the preparation of alkaline earth metal salts of (6R)-N(10)-formyl-5,6,7,8-tetrahydrofolic acid. An alkaline earth metal salt, either in the form of a solid, or in the form of an aqueous solution, is added, preferably under an inert gas atmosphere, to an ammonium salt or alkali metal salt of (6RS)-N(10)-formyl-5,6,7,8-tetrahydrofolic acid dissolved in water or an aqueous buffer solution. II is added an alkaline earth metal salt either in the form of a solid or in the form of an aqueous solution. The obtained mixture is allowed to crystallize, and the obtained solid is separated. The product is known to be cytostatic.

10 Claims, No Drawings

PROCESS FOR THE PREPARATION OF ALKALINE EARTH METAL SALTS OF (6R)-N(10)-FORMYL-5,6,7,8-TETRAHYDROFOLIC ACID

The present invention is directed to a process for the preparation of alkaline earth metal salts of (6R)-N(10)-formyl-5,6,7,8-tetrahydrofolic acid.

BACKGROUND OF THE INVENTION

Processes for the preparation of reduced folates having an uniform (6S)- or (6R)-configuration are described in the French patent application No. 90 03032 having the publication-No. 2 659 330 (which corresponds to U.S. Pat. No. 5,239,074). Herein is also described the further prior art.

Herein below the abbreviation THF is used for 5,6,7,8-tetrahydrofolic acid.

It is known that the hydrolysis of N(5),N(10)-methenyl-THF.Cl- in an aqueous buffer at a neutral or basic pH-value leads to N(10)-formyl-THF; see D. R. Robinson, Methods in Enzymology (1971) Vol XVIII, Part B [184], and G. K. Smith, P. A. Benkovic, S. J. Benkovic, Biochem. (1981), 20, 4034, and J. C. Rabinowitz, Methods in Enzymology (1963), 6, 814.

It is also known that N(10)-formyl-THF can be transformed thermically in N(5)-formyl-THF; see D. R. Robinson, supra.

When a pure diastereoisomer of N(5),N(10)-methenyl-THF.Cl- is hydrolized, then the corresponding pure diastereoisomer of N(10)-formyl-THF is obtained; see G. K. Smith et al, supra.

It is now surprisingly found now quite surprisingly that the addition of an alkaline earth metal salt to an ammonium salt or an alkali metal salt of a mixture of diastereoisomers of (6RS)-N(10)-formyl-THF dissolved in water, or in an aqueous buffer solution, leads to the selective crystallization of the alkaline earth metal salts of (6R)-N(10)-formyl-THF.

SUMMARY OF THE INVENTION

Accordingly, the invention, among other things, is directed to a process for the preparation of alkaline earth metal salts of (6R)-N(10)-formyl-5,6,7,8-tetrahydrofolic acid.

More particularly, the inventive process is directed to the preparation of alkaline earth metal salts of (6R)-N(10)-formyl-5,6,7,8-tetrahydrofolic acid of the following formula I.

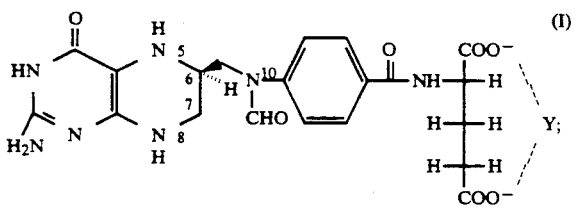

wherein Y is an alkaline earth metal cation, preferably $Ca^{2+}$,

The process comprises adding an alkaline earth metal salt, either in the form of a solid or in the form of an aqueous solution, preferably under an inert atmosphere, to an ammonium salt or alkali metal salt of (6RS)-N(10)-formyl-5,6,7,8-tetrahydrofolic acid of the following formula II

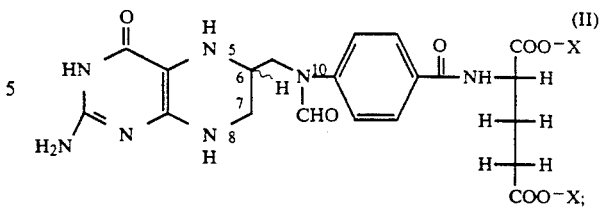

wherein X is an alkali metal cation or $NH_4^+$, dissolved in water or in an aqueous buffer solution.

The obtained mixture is then allowed to crystallize, and the obtained solid having the formula I is then separated.

DETAILED DESCRIPTION OF THE PREFERRED EMBODIMENTS

As noted above, the process of the invention comprises adding an alkaline earth metal salt, either in the form of a solid or in the form of an aqueous solution, preferably under an inert atmosphere, to an ammonium salt or alkali metal salt of (6RS)-N(10)-formyl-5,6,7,8-tetrahydrofolic acid of formula (II), wherein X is an alkali metal cation or $NH_4^+$, dissolved in water or in an aqueous buffer solution. The obtained mixture is then allowed to crystalline, and the obtained solid having formula (I) is separated.

Water used in the aforementioned process is preferably deionized water and/or degassed water. The buffer should give no precipitation with an alkaline earth metal salt, and is preferably tris-hydroxymethyl-aminomethane-hydrochloride.

The alkaline earth metal salt is preferably added under temperature conditions of from 20° to 60° C., more preferably about 30° C.

Crystallization is preferably carried out under temperature conditions of from 20° to 40° C., more preferably 30° C.

The alkaline earth metal salt is preferably an alkaline earth metal halide, more preferably a calcium halide, particularly calcium chloride, or an alkaline earth metal acetate.

Another aspect of the invention involves the use of compounds of formula (I) prepared according to the invention, for the preparation of (6R)-N(5),N(10)-methenyl-THF, (6S)-N(5)-methyl-THF and (6S)-N(5)-formyl-THF.

For identification of the diastereoisomeric purity the compound (6R)-N(10)-formyl-THF.$Ca^{2+}$ prepared according to the inventive process, the compound can be transformed into (6S)-N(5)-methyl-THF according to the process described in French patent application No. 90 03032 having the publication number 2 659 330. An analysis on a chiral HPLC-column (RESOLVOSIL column) will give a diastereoisomeric purity from 80 to 90%.

The diastereoisomeric pure compounds prepared according to the present invention can be transformed into (6S)-N(5)-formyl-THF according to the above mentioned article of D. R. Robinson.

The diastereoisomeric pure compounds prepared according to the present invention can also be transformed into (6R)-N(5),N(10)-methenyl-THF under acidic conditions according to known processes such as the above mentioned article of J. C. Rabinowitz.

(6R)-N(5),N(10)-Methenyl-THF can also be reduced to (6S)-N(5)-Methyl-THF according to known processes; see White, Bailey, Goldman, J. Biol. Chem. (1978), 253, 242.

The following example illustrates the present invention.

EXAMPLE

To 200 ml of an aqueous 0,2N solution of tris-hydroxymethyl-amino-methan-hydrochloride, which was adjusted to a pH-value of 8.3 with hydrochloric acid, there were added, under stirring at room temperature and under an argon atmosphere simultaneously and in portions, 15 g of (6RS)-N(5),N(10)-methenyl-THF.Cl⁻ and sufficient 20% aqueous NaOH, in order to obtain a clear solution having a pH-value of 8.3. This solution was warmed to a temperature of 30° C., 3.7 g of $CaCl_2.2H_2O$ were dissolved in a little bit of water (about 10 ml), and were added to the above mentioned solution.

After a few minutes a spontaneous crystallisation began. The mixture was stirred at the same temperature for two hours. The crystalline solid was filtered off, washed once with water, once with 94% ethanol and once with acetones and dried under reduced pressure at a temperature of 60° C.

5.5 g of white crystals of (6R)-N(10)-formyl-THF.$Ca^{2+}$ were obtained.

The HPLC-analysis on a reversed phase column showed a 98% chemical purity.

MS [FAB/matrix: Thioglycerin]: m+: 512, corresponding to the summation formula $C_{20}H_{21}N_7O_7Ca$.

IR (KBr): 3407, 3345, 3220, 1660, 1635, 1605, 1575, 1545, 1505, 1455, 1425, 1410, 1360, 1330 $cm^{-1}$.

For the identification of the diastereoisomeric purity, 15 mg of the above mentioned crystals were dissolved in 1.5 ml of a 1.8% solution of p-toluenesulfonic acid. Then 6 mg of $NaBH_3CN$ were added, and the mixture was stirred for 30 minutes at room temperature. Thereby (6R)-N(10)-formyl-THF was completely transformed into (6S)-N(5)-methyl-THF. The analysis of the later compound by means of a chiral HPLC-column (RESOLVOSIL) showed a diastereoisomeric purity of 85%.

We claim:

1. A process for preparing an alkaline earth metal salt of (6R)-N(10)-formyl-5,6,7,8-tetrahydrofolic acid of the following formula (I):

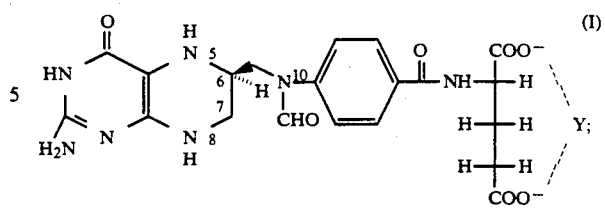

wherein Y is $Ca^{2+}$ or $Mg^{2+}$, said process comprising:
(i) under an inert atmosphere and temperature conditions of about 20° C. to about 60° C., adding a calcium or magnesium halide or acetate, either in the form of an aqueous solution or a solid, to an ammonium salt of, or alkali metal salt of, (6RS)-N(10)-formyl-5,6,7,8-tetrahydrofolic acid dissolved in water or in an aqueous buffer solution, said salt of (6RS)-N(10)-formyl-5,6,7,8-tetrahydrofolic acid having the following formula (II):

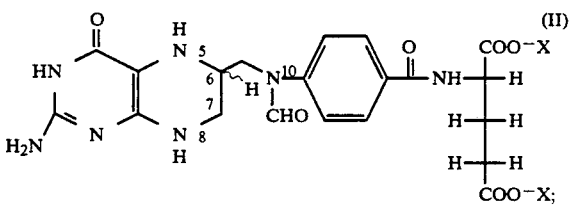

wherein X is an alkali metal cation or $NH_4^+$;
(ii) under temperature conditions of about 20° C. to about 40° C., allowing the mixture obtained from step (i) to crystallize; and
(iii) separating a solid obtained from step (ii), said solid characterized by formula (I).

2. A process according to claim 1, wherein Y is $Ca^{2+}$.

3. A process according to claim 1, wherein the alkaline earth metal salt is added at a temperature of about 30° C.

4. A process according to claim 1, wherein crystallization is carried out at a temperature at about 30° C.

5. A process according to claim 1, wherein the ammonium salt or alkali metal salt of (6RS)-N(10)-formyl-5,6,7,8-tetrahydrofolic acid is dissolved in at least one of deionized water and degassed water.

6. A process according to claim 1, wherein the ammonium salt or alkali metal salt of (6RS)-N(10)-formyl-5,6,7,8-tetrahydrofolic acid is dissolved in a buffer solution.

7. A process according to claim 1, wherein the buffer of the aqueous buffer solution having dissolved therein an ammonium salt of, or alkali metal salt of, (6RS)-N(10)-formyl-5,6,7,8-tetrahydrofolic acid, is trishydroxylmethyl-amino-methane-hydrochloride.

8. A process according to claim 1, wherein said calcium or magnesium halide or acetate is a calcium or magnesium halide.

9. A process according to claim 8, wherein the calcium or magnesium halide is a calcium halide.

10. A process according to claim 9, wherein the calcium halide is calcium chloride.

* * * * *